(12) United States Patent
Hyun et al.

(10) Patent No.: US 11,471,563 B2
(45) Date of Patent: *Oct. 18, 2022

(54) PREPARING METHOD OF NERVE CONDUITS

(71) Applicant: Wiregene Co., Ltd., Chungcheongnam-do (KR)

(72) Inventors: Jung Keun Hyun, Chungcheongnam-do (KR); Kwang-Ho Lee, Seoul (KR); Jin Ho Lee, Daejeon (KR); Jun-Hyeog Jang, Incheon (KR); Jonathan Campbell Knowles, St. Albans (GB); Dong-Wook Han, Busan (KR)

(73) Assignee: Wiregene Co., Ltd., Chungcheongnam-do (KR)

( * ) Notice: Subject to any disclaimer, the term of this patent is extended or adjusted under 35 U.S.C. 154(b) by 222 days.

This patent is subject to a terminal disclaimer.

(21) Appl. No.: 15/796,988

(22) Filed: Oct. 30, 2017

(65) Prior Publication Data

US 2018/0126038 A1    May 10, 2018

(30) Foreign Application Priority Data

Nov. 4, 2016 (KR) .................. 10-2016-0146703
Nov. 17, 2016 (KR) .................. 10-2016-0153483
Oct. 26, 2017 (KR) .................. 10-2017-0140472

(51) Int. Cl.
| | |
|---|---|
| *A61L 27/56* | (2006.01) |
| *A61L 27/38* | (2006.01) |
| *A61B 17/11* | (2006.01) |
| *A61L 27/14* | (2006.01) |
| *A61F 2/04* | (2013.01) |
| *A61L 27/58* | (2006.01) |

(52) U.S. Cl.
CPC ........ *A61L 27/383* (2013.01); *A61B 17/1128* (2013.01); *A61F 2/04* (2013.01); *A61L 27/14* (2013.01); *A61L 27/58* (2013.01); *A61B 2017/1132* (2013.01); *A61L 2430/32* (2013.01)

(58) Field of Classification Search
None
See application file for complete search history.

(56) References Cited

U.S. PATENT DOCUMENTS

| | | | | |
|---|---|---|---|---|
| 2010/0076465 A1* | 3/2010 | Wiberg | .............. | A61B 17/1128 606/152 |
| 2011/0129515 A1* | 6/2011 | Archibald | ............... | A61L 27/24 424/426 |
| 2013/0190687 A1* | 7/2013 | Kokai | ..................... | A61L 27/18 604/93.01 |

FOREIGN PATENT DOCUMENTS

KR    10-2015-0105826    9/2015

OTHER PUBLICATIONS

Hyun et al (KR 20150105826; wherein a machine translation is provided) (Year: 2015).*
Oh et al (Peripheral nerve regeneration within an asymmetrically porous PLGA/Pluronic F127 nerve guide conduit. Biomaterials 29 (2008) 1601-1609) (Year: 2008).*

* cited by examiner

*Primary Examiner* — Jake M Vu

(57) ABSTRACT

The present disclosure relates to a method for preparing a nerve conduit, more particularly to a method for preparing a porous nerve conduit having micropores formed in microchannels and the nerve conduit prepared according to the present disclosure can be usefully used in in-vitro and in-vivo researches on nerves.

18 Claims, 11 Drawing Sheets

✓ Small animal study & *in vitro* study

✓ Large animal study & *in vitro* study

- Diameter : 2.2 mm
- Average diameter of microchannels : 20.76 ± 0.80 μm
- Number of microchannels : 14435 ± 1830.25

Scale Bar = 500 um
Arrows = regenerating axons

Scale Bar = 500 um
Arrows = regenerating axons

PREPARING METHOD OF NERVE CONDUITS

CROSS-REFERENCE TO RELATED APPLICATION

This application claims priority of Korean Patent Application No. 10-2016-0146703, filed on Nov. 4, 2016, priority of Korean Patent Application No. 10-2016-0153483, filed on Nov. 17, 2016, and priority of Korean Patent Application No. 10-2017-0140472, filed on Oct. 26, 2017, in the KIPO (Korean Intellectual Property Office), the disclosure of which is incorporated herein entirely by reference. The invention of this application was made by inventor(s) including Jung Keun Hyun to a joint research agreement that was in effect before the effective filing date of the claimed invention. The claimed invention of this application was made as a result of activities undertaken with the scope of the joint research agreement. The joint research agreement applies to this application and Application Ser. Nos. 15/797,063; 15/797,012; 15/650,436.

BACKGROUND OF THE INVENTION

Field of the Invention

The present disclosure relates to a method for preparing a nerve conduit, more particularly to a method for preparing a porous nerve conduit having micropores formed in microchannels.

Description of the Related Art

When a peripheral nerve is damaged due to injury, the sections of the cut nerve are connected with each other directly. However, such anastomosis is almost impossible for most nerves. In this case, autogenous nerve grafting is conducted to restore its function. However, the autogenous nerve grafting is problematic in that it is difficult to match the thickness and shape of the nerve tissue of the damaged area and the grafted nerve tissue, the nerves that can be taken for the grafting are limited and the decline in function can occur at the area where the grafted nerve is taken. Therefore, a nerve conduit is used to restore the function of a damaged nerve.

The nerve conduit connects both ends of the damaged nerve and serves as a means of guiding nerve regeneration. The both ends of the damaged nerve are fixed inside the nerve conduit to induce the connection of the nerve in the conduit. When the nerve conduit is used, it is advantageous in that the infiltration of scar tissue interfering with nerve regeneration can be prevented, nerve regeneration can be induced along a desired direction, the nerve regeneration promoting substances secreted from the nerve itself is maintained inside the conduit and the substances interfering with the regeneration can be blocked.

The nerve conduit should be biocompatible to avoid tissue rejection and should be biodegraded after nerve regeneration so that the removal of the nerve conduit is unnecessary after the nerve regeneration. Also, the degradation product of the nerve conduit should be nontoxic in the body.

In addition, the nerve conduit should have the mechanical property to maintain the inside space during the nerve regeneration. The nerve conduit should have suitable flexibility and tensile strength so that the end portion of the nerve conduit can be maintained stably after the insertion of the nerve conduit. Also, the nerve conduit should be able to prevent damage to nearby normal tissues and should be easily transplantable.

As the material of the nerve conduit, natural polymers such as collagen, chitosan, etc. and synthetic polymers such as silicone, polylactic acid (PLA), polyglycolic acid (PGA), poly(lactic-co-glycolic acid) (PLGA), polycaprolactone, etc. are available.

Among them, collagen is the most frequently used natural polymer material. Collagen has been frequently used as the material of the nerve conduit for nerve regeneration due to excellent biocompatibility and weak antigenicity. However, the use of collagen is problematic in that it has to be extracted from an animal and large-scale production is difficult because its storage is complicated. Also, it costs a lot to prepare the nerve conduit using collagen. In addition, the nerve conduit prepared from collagen is limited in clinical application because of weak tensile strength.

The synthetic polymers such as PLA, PLGA, etc. have been verified to be biocompatible. A nerve conduit based on these synthetic polymers has superior structural stability and tensile strength because it is formed as a tube without pores (small holes). However, the synthetic polymer-based nerve conduit is problematic in that control of physical properties is difficult. In addition, the synthetic polymer-based nerve conduit known thus far is disadvantageous in that the exchange of body fluid is not achieved easily.

Korean Patent Application No. 2014-0027854 discloses a method for preparing a synthetic polymer-based nerve conduit using glass fibers. However, the nerve conduit still has the problem that the exchange of body fluid is difficult because it is in the form of a polymer tube without pores.

As described above, the nerve conduit is prepared from a biocompatible material. It is necessary to measure the time required for degradation of the biocompatible material. In general, the biodegradation of the biodegradable nerve conduit prepared from the biomaterial is determined by measuring weight change.

However, the weight of the biomaterial varies greatly depending on the moisture remaining in the material. For a nerve conduit having an internal structure, additional data are required regarding how the initial internal structure is changed as the nerve conduit is degraded. However, such information is not enough.

In order to solve these problems, the inventors of the present disclosure have researched on a porous nerve conduit having microchannels and a microporous structure at the same time and have completed the present disclosure. The inventors of the present disclosure have also researched on a nerve conduit containing a fluorescent nanoparticle and have completed the present disclosure.

SUMMARY OF THE INVENTION

The present disclosure is directed to providing a method for preparing a porous nerve conduit having microchannels and a microporous structure at the same time.

The present disclosure is also directed to providing a porous nerve conduit prepared by the preparation method.

The present disclosure provides a method for preparing a porous nerve conduit, including: a step of preparing a polymer material for a nerve conduit by dissolving a hydrophobic biocompatible polymer in a water-miscible organic solvent; and a step of preparing a nerve conduit formed of a porous polymer having micropores formed in a hydrophobic polymer by immersing the polymer material for a nerve conduit in a hydrophilic solution and thereby separating the organic solvent from the polymer material.

The porous nerve conduit may be for regeneration of a central nerve or a peripheral nerve.

The nervous system of higher animals is classified into the central nervous system, the peripheral nervous system and the autonomic nervous system. The central nervous system is a nervous system including the brain and spinal cord. The peripheral nervous system is a nervous system which diverges from the central nervous system such as the brain and spinal cord and is distributed throughout the body like branches.

In general, when the axon of the neuron constituting the peripheral nervous system is physically damaged, it regenerates normally and restores its function with time. However, when the peripheral nerve is damaged due to accidents, surgery, etc., social activities may be severely affected. In particular, when the nerves of the hands or feet are cut, it is difficult to connect them. For the central nervous system, neuronal damage leads to permanent loss of function.

When the peripheral nerve is cut, the cut nerve grows at the peripheral site at a speed of about 1 mm per day. Therefore, the cut nerve can be regenerated by introducing a tube-type nerve conduit to the cut site.

The nerve conduit serves as a passage for connecting the broken nerve tissue and regenerating nerve fibers. Accordingly, when both ends of the cut nerve are connected to the nerve conduit, the nerve may be regenerated as nerve fiber grows at one side of the nerve inside the nerve conduit. In addition, the nerve conduit provides a controlled microenvironment and the growth of axon may be promoted as neurotrophic factor ecreted from the damaged nerve are concentrated in the conduit.

It is known that the central nerve such as the spinal cord, etc. cannot be regenerated once it is damaged by injury such as a traffic accident or by cerebrovascular accident, which is contrasted with the peripheral nerve. Because the central nerve cannot be regenerated once it is damaged, the damage to the central nerve often leads to partial or complete paralysis.

The damaged central nerve can be regenerated by using the nerve conduit. An example is as follows. When both ends of a damaged spinal nerve are connected by the nerve conduit, the central nerve may be regenerated as the nerve grows inside the nerve conduit. A nerve conduit having micropores as in the present disclosure facilitates the growth of axon because the neurotrophic factor secreted from the damaged nerve are secreted well inside the nerve conduit too. In particular, the nerve conduit according to the present disclosure allows easy nerve generation under an environment without additional factors such as Schwann cells, etc.

Accordingly, the porous nerve conduit of the present disclosure allows nerve generation by using the nerve conduit only without the need of additionally attaching cells or regeneration factors to the nerve conduit. Regeneration of the peripheral nerve or the central nerve is possible by using the nerve conduit of the present disclosure. Although it is known that the regeneration of the central nerve is almost impossible, not only the peripheral nerve but also the central nerve can be regenerated by using the nerve conduit of the present disclosure.

In the present disclosure, the term "hydrophobic biocompatible polymer" refers to a polymer which is biocompatible, biodegradable and insoluble in water.

As the hydrophobic biocompatible polymer, any hydrophobic biocompatible polymer commonly used in the related art may be used without limitation. Specifically, one or more selected from a group comprising of polylactic acid (PLA), poly-L/D-lactide (PLDA), poly-L-lactic acid (PLLA), polyglycolic acid (PGA)), polydioxanone, polyhydroxybutyrate (PHB), polyhydroxyalkanoate (PHA) poly(lactic-co-glycolic acid) (PLGA), polycaprolactone (PCL), a copolymer thereof and a mixture thereof may be used, although not being necessarily limited thereto.

In the present disclosure, the term "water-miscible organic solvent" refers to an organic solvent which is miscible at least partly with water or completely with water.

As the water-miscible organic solvent, any water-miscible organic solvent used in the related art may be used without limitation. Specifically, it may be selected from a group comprising of ethanol, isopropyl alcohol, N-methyl-2-pyrrolidone, 2-pyrrolidone, glycerol, propylene glycol, polyethylene glycol, tetraglycol, glycerol formal, ethyl acetate, ethyl lactate, diethyl carbonate, propylene carbonate, acetone, methyl ethyl ketone, dimethyl sulfoxide, dimethyl sulfone, tetrahydrofuran, tetrahydrofurfuryl alcohol, succinic acid diethyl ester, triethyl citrate, dibutyl sebacate, dimethylacetamide, lactic acid butyl ester, propylene glycol diacetate, diethylene glycol monoethyl ether and a mixture thereof, although not being necessarily limited thereto. More specifically, it may be N-methyl-2-pyrrolidone, tetraglycol or dimethyl sulfoxide, although not being necessarily limited thereto.

The "polymer material" refers to a hydrophobic biocompatible polymer dissolved in a water-miscible solvent.

In an exemplary embodiment of the present disclosure, a PLGA-TG or PCL-TG solution prepared by using poly(lactic-co-glycolic acid) (PLGA) or polycaprolactone (PCL) as the hydrophobic biocompatible polymer and tetraglycol (TG) as the water-miscible solvent is used as the polymer material. In particular, when the polymer material is prepared by mixing PLGA with TG, it is advantageous in that a process of dissolving the polymer material again can be omitted because a solution state is maintained at room temperature after the PLGA is dissolved with the TG.

By immersing the polymer material for a nerve conduit in the hydrophilic solution and thereby separating the organic solvent from the polymer material, a nerve conduit formed of a porous hydrophobic polymer having micropores formed may be obtained.

A detailed description is given as follows. When the polymer material for a nerve conduit formed of the hydrophobic biocompatible polymer and the water-miscible organic solvent is immersed in the hydrophilic solution, micropores are formed in the polymer as the organic solvent is released from the polymer, i.e., as the organic solvent is phase-separated.

In the present disclosure, the hydrophilic solution includes water, although not being limited thereto.

In the present disclosure, the term "micropore" refers to a very small nano-sized hole. In the present disclosure, the micropore refers to a very small nano-sized hole with a size of 1 μm or smaller.

The polymer material for a nerve conduit may be one in which the hydrophobic biocompatible polymer is dissolved in the water-miscible organic solvent at a concentration of 10-40 weight/volume % (w/v %), specifically 10-25 w/v %, more specifically 15-25 w/v %, most specifically 20 w/v %.

The term "weight/volume % (w/v %)" refers to the weight (g) of the hydrophobic polymer dissolved in 100 mL of the organic solvent.

If the concentration is below 10 w/v %, porosity may increase due to the excessive use of the water-miscible organic solvent. And, if the concentration exceeds 40 w/v %, enough micropores may not be formed.

And, in the step of preparing the polymer material for a nerve conduit, after the hydrophobic biocompatible polymer is dissolved in the organic solvent, a polymer material for a nerve conduit containing a fluorescent nanoparticle may be prepared by further adding a nanoparticle.

The term "nanoparticle" refers to a nano-sized particle. The nano size includes the range of size understood by those of ordinary skill in the related art. Specifically, the nano size may be 0.1-1000 nm, more specifically 10-1000 nm, more specifically 300-700 nm, more specifically 20-500 nm, more specifically 40-250 nm.

The nanoparticle may include any nanoparticle used in the related art. Specifically, the nanoparticle may be a fluorescent nanoparticle, although not being necessarily limited thereto.

The term "fluorescent nanoparticle" refers to a nanoparticle which continuously emits fluorescence of a predetermined intensity.

As the fluorescent nanoparticle, any fluorescent nanoparticle used for fluorescence imaging known in the related art may be used without limitation. Specifically, a fluorescent nanoparticle prepared from a material which does not exhibit toxicity in the body may be used, although not being necessarily limited thereto.

The fluorescent nanoparticle may have a size of 300-700 nm, although not being necessarily limited thereto.

In an exemplary embodiment of the present disclosure, a nerve conduit is prepared using a silica-based nanoparticle which emits green fluorescence.

In another aspect, the present disclosure provides a method for preparing a porous nerve conduit having a microchannel structure with micropores formed, including: a step of inserting a plurality of glass fibers into a container having upper and lower channels; a step of injecting a polymer material for a nerve conduit containing a hydrophobic biocompatible polymer and a water-miscible organic solvent into the container in which the plurality of glass fibers are inserted; a step of infiltrating the polymer material between the glass fibers by applying vacuum to the upper channel; a step of separating the glass fibers with the polymer material infiltrated from the container; and a step of dissolving the glass fibers by immersing the separated glass fibers in a hydrophilic solution, wherein the polymer material for a nerve conduit is one in which the hydrophobic biocompatible polymer is dissolved in the water-miscible organic solvent at a concentration of 10-40 weight/volume % (w/v %) and, in the step of dissolving the glass fibers, microchannels are formed as the hydrophobic biocompatible polymer is cured and micropores are formed in the microchannels formed of the hydrophobic polymer as the water-miscible organic solvent is mixed with the hydrophilic solution and released from the hydrophobic polymer.

The term "microchannel" refers to a void space with a size of 5-20 μm formed as the glass fibers are dissolved and means a channel with a microstructure formed inside the nerve conduit. The microchannel guides the growth of axons along a desired direction and prevents infiltration of scar tissue which interferes with nerve regeneration. In addition, a structure capable of drug delivery, etc. may be provided by attaching nerve regeneration factors, etc. to the microchannels formed inside the nerve conduit.

The nerve conduit of the present disclosure may have about 1000-10000 channels. But, it may also contain more channels.

The present disclosure provides a method for preparing a porous nerve conduit having micropores formed in microchannels. The processes of forming the microchannels and the micropores are described in detail as follows.

The polymer material for a nerve conduit formed of the hydrophobic biocompatible polymer and the water-miscible organic solvent is infiltrated between the space of the glass fibers filled in the container (e.g., a glass tube). Because the space between the glass fibers is narrow, the polymer material may be infiltrated by using negative pressure or positive pressure. After the polymer material is filled between the glass fibers, the glass fibers and the polymer material are separated from the container and immersed in the hydrophilic solution. Then, microchannels are formed in the space that has been occupied by the glass fibers as the glass fibers are dissolved and micropores are formed as the water-miscible organic solvent is released from the polymer material. Specifically, when the glass fibers are dissolved in the hydrophilic solution (e.g., water) and the water is contacted with the hydrophobic polymer, microchannels are formed as the polymer having hydrophobic property is cured. And, when water is introduced into the newly formed microchannels, micropores are formed as the water-miscible organic solvent is mixed with the water and released from the hydrophobic polymer, i.e., as the organic solvent is phase-separated.

The nerve conduit prepared according to the present disclosure allows easy body fluid exchange in vivo due to the microchannels having the micropores formed.

In the polymer material for a nerve conduit, a nanoparticle may be further added in addition to the hydrophobic polymer and the water-miscible organic solvent.

The nanoparticle may include any nanoparticle used in the related art. Specifically, the nanoparticle may be a fluorescent nanoparticle, although not being necessarily limited thereto.

The lower channel may have a smaller diameter than the upper channel and the container may be sloped with a discontinuous angle.

Because the lower channel has a smaller diameter than the upper channel, the glass fibers injected into the container may remain filled inside the container without flowing out.

The container may be sloped with a discontinuous angle. More specifically, the container may have the upper and lower channels formed to be sloped with a discontinuous angle.

Due to the container sloped with a discontinuous angle and the upper and lower channels thereof, the glass fibers inserted into the container have constant intervals and the microchannels formed in the space where the glass fibers have been dissolved also have constant intervals. That is to say, because the porous nerve conduit prepared according to the present disclosure has microchannels formed with constant intervals, nerve regeneration can be induced along the same direction.

The upper channels and the lower channels of the container may be formed by heating the center portion of the glass tube and thereby forming a bottleneck, although not being limited thereto.

The polymer material for a nerve conduit may be in a solution state at room temperature.

In the present disclosure, the "room temperature" means a temperature of 15-25° C.

The method for preparing a porous nerve conduit having a microchannel structure with micropores formed may further include, after the step of dissolving the glass fibers: a step of cooling a nerve conduit formed after the glass fibers are dissolved with liquid nitrogen; and a step of shaping the cooled nerve conduit by cutting.

The container may be formed of a transparent material so that the infiltration of the polymer material for a nerve conduit can be checked visually. Specifically, the transparent material may be glass, although not being necessarily limited thereto.

The application of vacuum may be repeated multiple times. Through this, a nerve conduit with a uniform density may be prepared. The application of vacuum into the container (e.g., a glass tube) may be repeated multiple times using a syringe, although not being necessarily limited thereto.

In another aspect, the present disclosure provides a porous nerve conduit having a microchannel structure with micropores formed, prepared by the preparation method described above.

The microchannels may be formed along the axis direction of the nerve conduit as the glass fibers are inserted into the container along the axis direction.

The microchannels may be formed as a polymer material for a nerve conduit formed of a water-miscible organic solvent and a hydrophobic biocompatible polymer reacts with a hydrophilic solution and the hydrophobic biocompatible polymer is cured and the micropores may be formed in the microchannels formed of the hydrophobic polymer as the water-miscible organic solvent is mixed with the hydrophilic solution and released from the hydrophobic biocompatible polymer.

In another aspect, the present disclosure provides a method for regenerating a nerve using the nerve conduit according to the present disclosure.

A nerve may be generated by transplanting the nerve conduit according to the present disclosure into a damaged nerve area. The nerve may be a peripheral nerve or a central nerve.

Specifically, the method for regenerating a nerve includes: a step of inserting the nerve conduit according to the present disclosure into a biocompatible polymer tube formed of a hydrophobic biocompatible polymer; and a step of transplanting the biocompatible polymer tube with the nerve conduit inserted into a damaged nerve area, wherein micropores are formed in the biocompatible tube.

The micropores may be formed in the biocompatible tube in a manner similar to the micropore preparation described above. Specifically, the glass tube is immersed in a mixture solution of a hydrophobic biocompatible polymer and a water-miscible organic solvent to form a thin coat on the surface of the glass tube. Then, when the coated glass tube is immersed in water, the hydrophobic biocompatible polymer is cured as it is contacted with water and micropores are formed in the hydrophobic polymer as the water-miscible organic solvent is mixed water and released from the hydrophobic polymer. The biocompatible tube may be obtained by pushing or pulling from the glass tube.

In an exemplary embodiment of the present disclosure, after inserting the glass fibers into the upper channels of the container (glass tube) along the axis direction, a polymer material (PLGA-TG solution) is injected into the container and infiltrated into the glass fibers by applying vacuum. Then, after separating the glass fibers from the container, the glass fibers are dissolved completely by immersing in water (DW). When the glass fibers are dissolved, microchannels are formed as the hydrophobic polymer is contacted with water and cured and micropores are formed in the microchannels. That is to say, the nerve conduit having microchannels with micropores formed in the axis direction is formed in the space where the glass fibers have been dissolved by inserting the glass fibers along the axis direction of the container and then dissolving the glass fibers.

In another exemplary embodiment of the present disclosure, a peripheral nerve and/or a central nerve can be regenerated using the prepared nerve conduit without having to use additional regeneration factors, cells, etc. that help nerve regeneration.

The porous nerve conduit prepared according to the present disclosure may be prepared to have various diameters and lengths. In addition, the diameter and the length of the nerve conduit of the present disclosure may be changed as desired when preparing the nerve conduit to be applicable to in-vitro and in-vivo researches on nerves.

The present disclosure provides the following effects.

According to a preparation method of the present disclosure, a polymer material in which a hydrophobic biocompatible polymer is dissolved in a water-miscible solvent is infiltrated between glass fibers and then immersed in a hydrophilic solution. Then, microchannels are formed as the hydrophobic polymer is contacted with the hydrophilic solution and cured, whereas micropores are formed in the hydrophobic biocompatible polymer as the water-miscible solvent is released from the polymer. The micropores allow exchange of body fluid.

As the hydrophobic biocompatible polymer is mixed with the water-miscible solvent, the melting point of the polymer solution is lowered. Therefore, after the hydrophobic biocompatible polymer is dissolved in the water-miscible solvent, the solution state is maintained at room temperature and a process of dissolving the polymer material again is unnecessary.

By infiltrating the polymer solution with a predetermined viscosity into the space between the glass fibers and repeatedly applying vacuum multiple times, a nerve conduit with a uniform density can be prepared.

A peripheral nerve and/or a central nerve can be regenerated using the nerve conduit according to the present disclosure without having to use additional regeneration factors, cells, etc. that help nerve regeneration.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
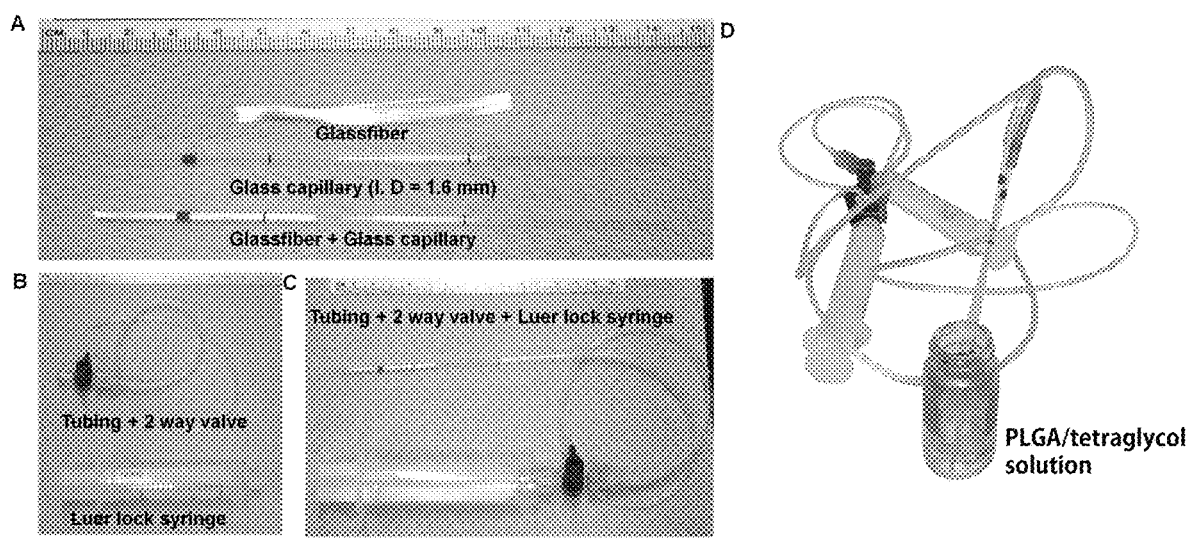
FIG. 1 shows photographs illustrating a method for preparing a porous nerve conduit. A shows glass fibers, a glass capillary and a glass capillary into which glass fibers are inserted, B shows a silicone tube coupled with a 2-way valve and a Luer lock syringe, C shows a silicone tube coupled with a 2-way valve and a Luer lock syringe, and D shows application of vacuum into a glass tube using a syringe.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

Example 1: Porous Nerve Conduit 1-1: Preparation of Porous PLGA Nerve Conduit

A 20% (w/v) PLGA-TG solution (polymer material) was prepared by mixing the hydrophobic polymer poly(lactic acid-co-glycolic acid) (PLGA) (lactic acid/glycolic acid mol %, 85:15) and the water-miscible solvent tetraglycol (TG) (density: 1.09 g/mL, Sigma-Aldrich, USA) at a weight/volume (w/v) ratio of 20% (w/v) and then dissolving at 60° C. for 18 hours.

A glass capillary with an inner diameter of 1.6 mm and a length of 13 cm was heated at the center portion to form a bottleneck, thereby forming upper and lower channels sloped with a discontinuous angle. The lower channels were formed to have smaller diameters than the upper channel. Then, 7000-8500 strands of a water-soluble glass fiber ($50P_2O_5$-$20CaO$-$30Na_2O$ in mol % (1100° C., 800 rpm)) with diameters of 10-20 µm were cut to 5-6 cm and inserted densely into the upper channels of the glass tube along the axis direction (FIG. 1A and FIG. 2A).

A pressure device was prepared by connecting a Luer lock syringe equipped with a silicone tube of an inner diameter of 0.8 mm and a length of 15 cm, coupled with a 2-way valve, to the upper channels of the glass fiber-inserted glass tube (FIG. 1B and FIG. 1C).

Figure 2:
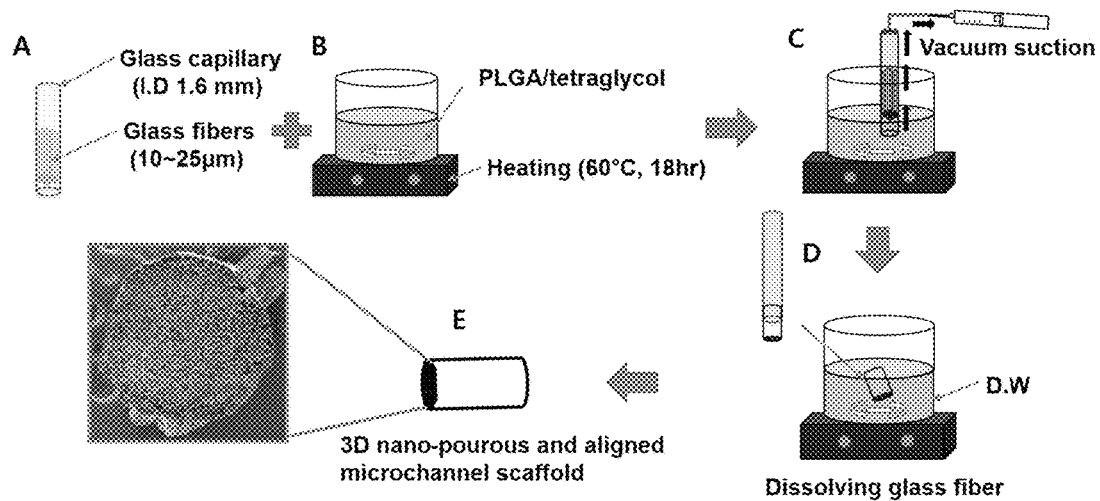
FIG. 2 schematically shows a method for preparing a porous nerve conduit.

After immersing the lower channels of the glass tube in the 20% (w/v) PLGA-TG solution at room temperature, vacuum was repeatedly applied into the glass tube using a syringe such that the 20% (w/v) PLGA-TG solution was completely infiltrated into the void space between the glass fibers (FIG. 1D and FIG. 2C).

Figure 3A:
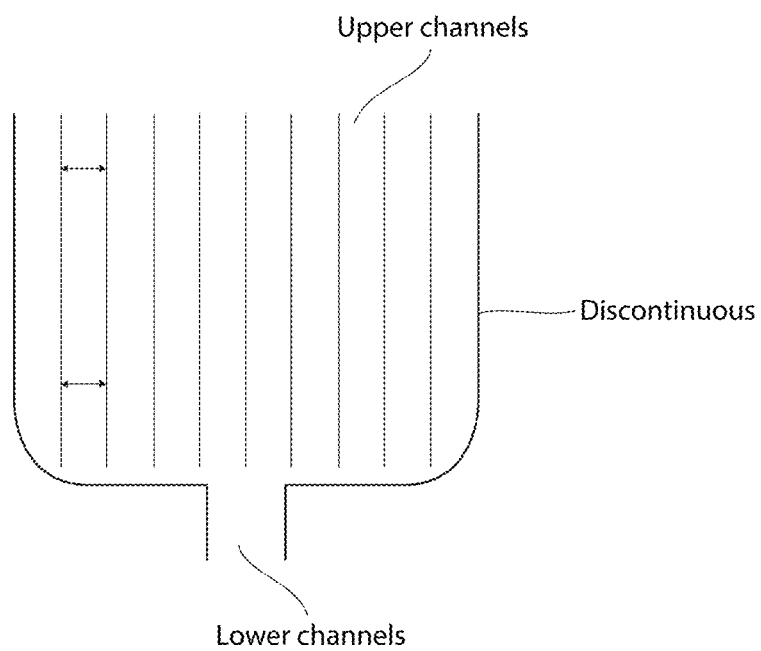
FIG. 3A and FIG. 3B show channel formation in a container with a discontinuous (a) or continuous (b) slope.
Figure 3B:
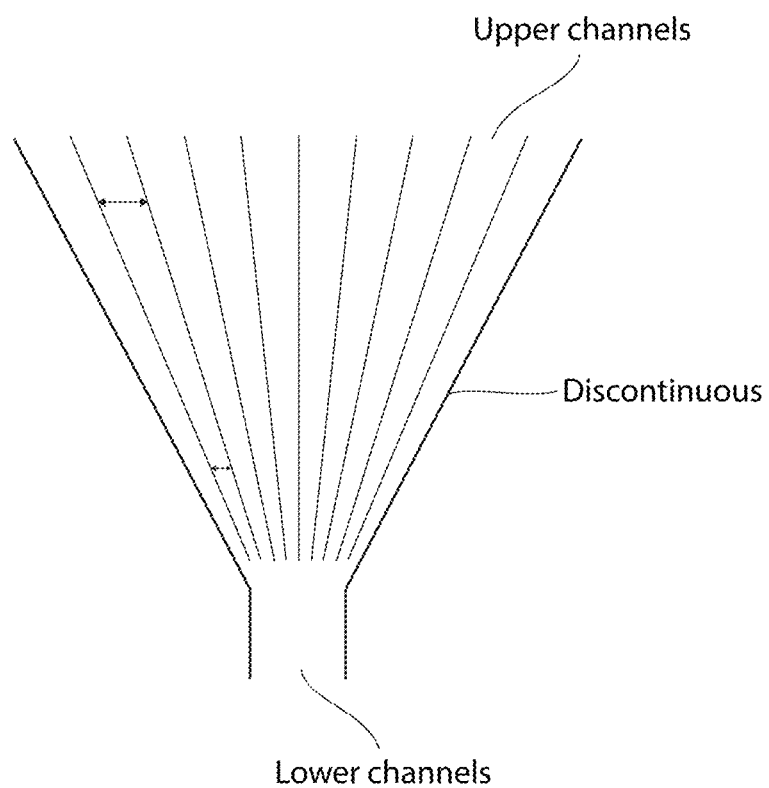

The specific configuration of the glass tube (container) is shown in FIG. 3A. As shown in FIG. 3A, the diameter of the lower channels was decreased than that of the upper channels with a discontinuous angle. If the angle is continuous (FIG. 3B), it is difficult to maintain constant intervals between the glass fibers because the intervals between the glass fibers decrease gradually.

If the nerve conduit is prepared in the state where the intervals between the glass fibers are not constant, the intervals between the microchannels of the nerve conduit will not be constant too. Then, the direction of nerve regeneration induced by the glass fibers will be different depending on the microchannel. As a result, it is difficult to induce nerve regeneration in the same direction.

Figure 4:
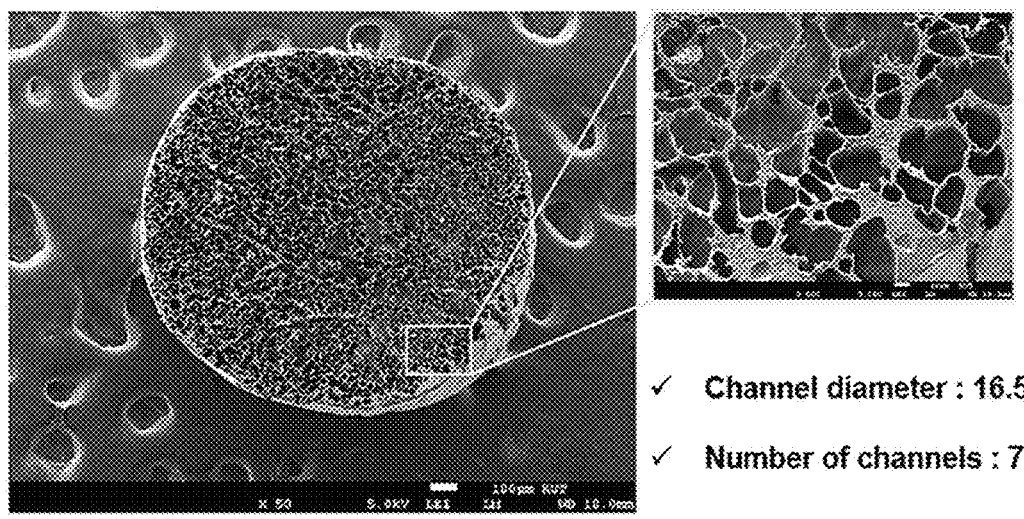
FIG. 4 shows transverse cross-sectional SEM images of a porous PLGA nerve conduit; scale bar=(left) 100 µm, (right) 10 µm.
Figure 5:
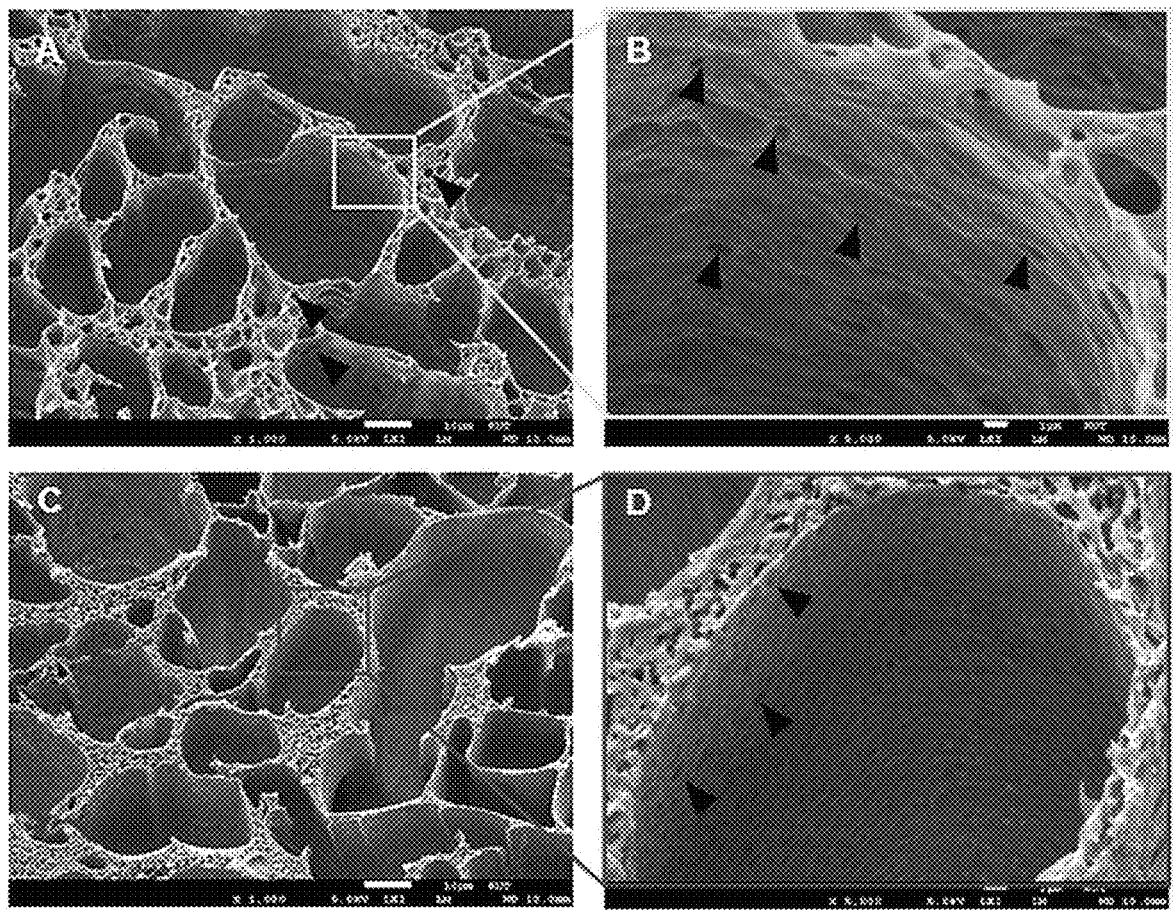
FIG. 5 shows magnified SEM images showing a microstructure at the transverse cross section of a porous nerve conduit; scale bar=(A, C) 10 µm, (B, D) 1 µm, ▶=micropores inside channel.
Figure 6:
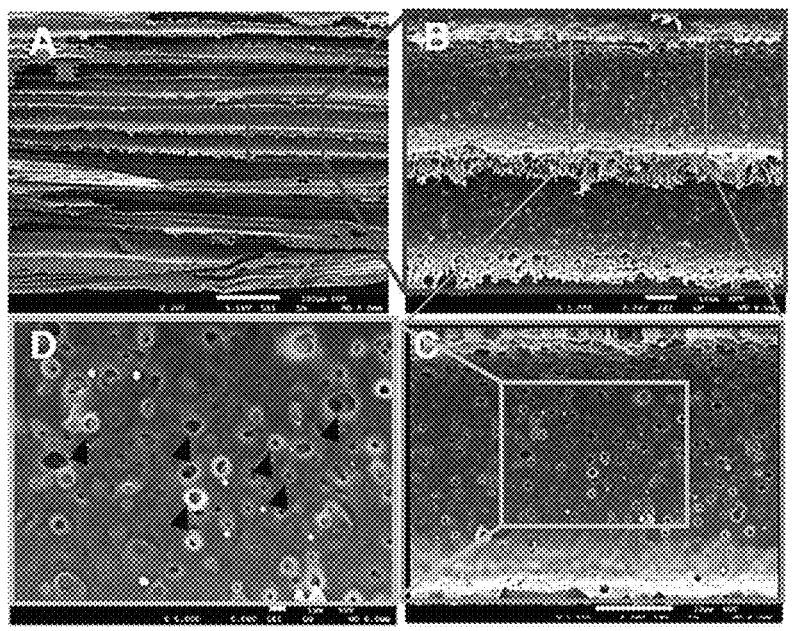
FIG. 6 shows longitudinal cross-sectional SEM images of a porous nerve conduit; scale bar=(A) 100 µm, (B) 10 µm, (C) 10 µm, (D) 1 µm, ▶=micropores inside channel.
Figure 7:
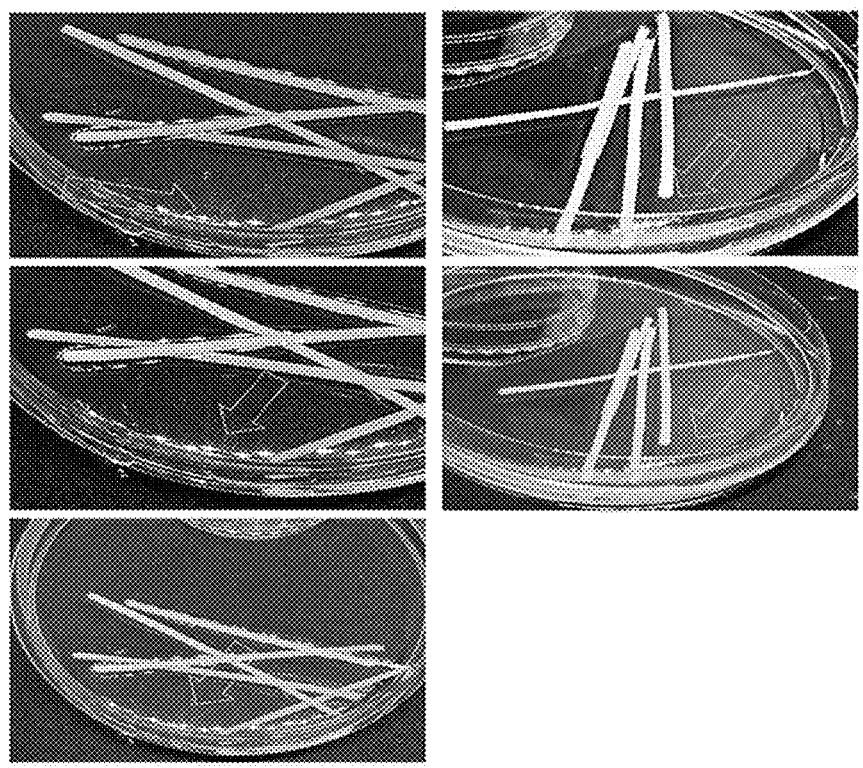
FIG. 7 shows TG released from a porous nerve conduit and submerged in distilled water (DW); arrow: TG.

The PLGA-TG solution-infiltrated glass fibers were separated from the glass tube using a wire with a diameter of 1.5 mm and a length of 15 cm and, immediately thereafter, completely immersed in distilled water (DW) at 10-20° C. for at least 24 hours (FIG. 2D), so that the glass fibers were completely dissolved, and about 7,000-8,500 (7,777±716.2) microchannels of PLGA, with diameters of 10-20 µm (16.54±3.6 µm), were formed in the space where the glass fibers had been dissolved (FIG. 2E and FIG. 4). The microchannels were formed as the glass fibers were dissolved in the water at 10-20° C. and the hydrophobic polymer PLGA was cured at the same time. Also, micropores were formed inside the microchannels as the glass fibers infiltrated with the PLGA-TG solution were as the TG was mixed with the water while they were immersed in the DW (FIG. 4, FIG. 5 and FIG. 6). Because the TG released from the nerve conduit had a higher density than the DW, it was submerged like heat haze in the DW (FIG. 7).

Figure 8:
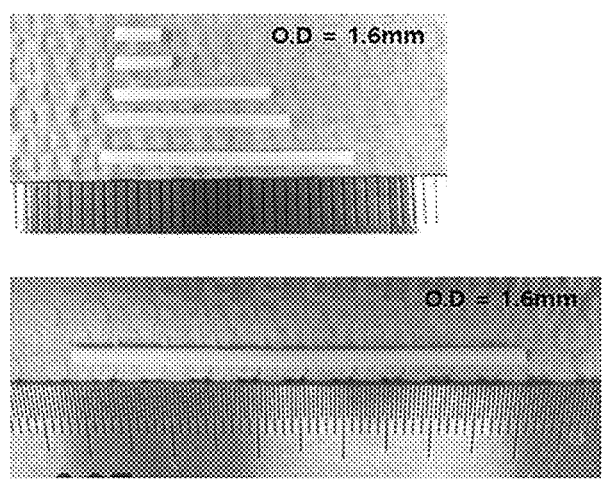
FIG. 8 shows porous nerve conduits prepared with various diameters and lengths depending on applications.
Figure 8:
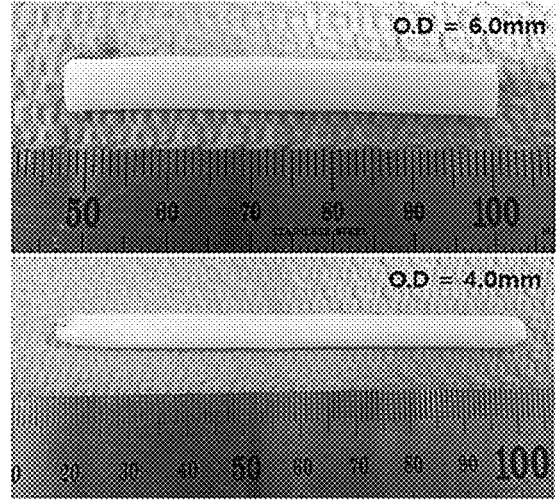

After the glass fibers and the TG were removed through the treatment with DW, the prepared porous microchannels formed of PLGA, i.e., the nerve conduit, was frozen in liquid nitrogen for about 30 seconds, cut to a desired size and then shaped into a desired shape (FIG. 8).

1-2: Investigation of Microstructure Inside Porous PLGA Nerve Conduit

The microstructure formed in the microchannels inside the nerve conduit manufactured in Example 1-1 was investigated by scanning electron microscopy (SEM) (FIG. 4, FIG. 5 and FIG. 6).

FIG. 4 shows the transverse cross section of the nerve conduit, FIG. 5 shows magnified images showing the microstructure at the transverse cross section of the nerve conduit and FIG. 6 shows the longitudinal cross section of the nerve conduit. It can be seen that the microchannels were formed continuously inside the nerve conduit and micropores were formed in the microstructure.

1-3:3D Micro-CT Imaging of Porous Nerve Conduit

Figure 9:
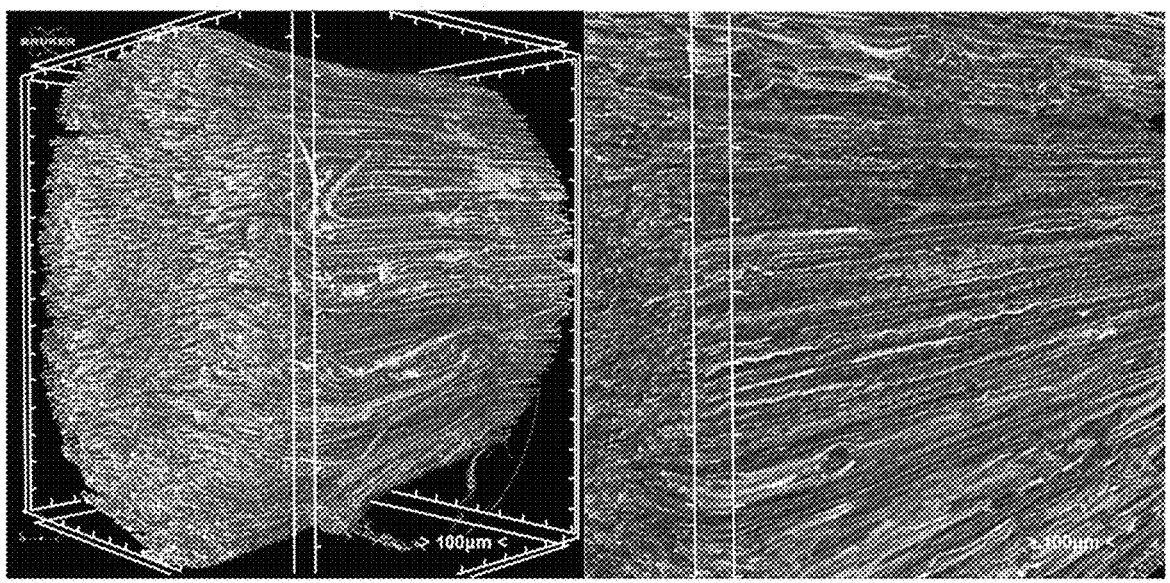
FIG. 9 shows 3D micro-CT images (sagittal plane) of a nerve conduit prepared according to an exemplary embodiment of the present disclosure.

The 3D CT images of the nerve conduit of Example 1-1 are shown in FIG. 9. Intact microchannels inside the nerve conduit are observed as seen from FIG. 9.

1-4: Preparation of Porous PCL Nerve Conduit

Figure 10:
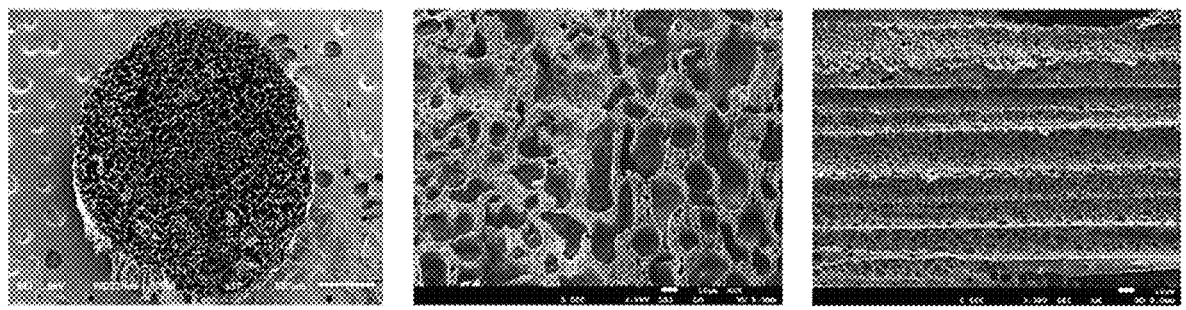
FIG. 10 shows transverse cross-sectional SEM images of a porous PCL nerve conduit; scale bar=(left) 500 µm, (center) 10 µm (right) 10 µm. A shows a transverse cross-sectional image, B shows a magnified transverse cross-sectional SEM images showing a microstructure and C shows a longitudinal cross-sectional image.

A porous nerve conduit was prepared in the same manner as in Example 1-1 except that the polymer material was prepared using polycaprolactone (PCL) as the hydrophobic biocompatible polymer material instead of the PLGA. As the polymer material, an 18% (w/v) PCL-TG solution was prepared by mixing PCL and TG at a weight/volume (w/v) ratio of 18% (w/v) and then dissolving at 90° C. for 18-24 hours. Then, a nerve conduit was prepared in the same manner as in Example 1-1 (FIG. 10).

Example 2: Porous Nerve Conduit Containing Fluorescent Nanoparticle 2-1: Preparation of Porous Nerve Conduit Containing Fluorescent Nanoparticle A 20% (w/v) PLGA-TG solution (polymer material) was prepared by mixing the hydrophobic polymer poly(lactic acid-co-glycolic acid) (PLGA) (lactic acid/glycolic acid mol %, 85:15) and the water-miscible solvent tetraglycol (TG) (density: 1.09 g/mL, Sigma-Aldrich, USA) at a weight/volume (w/v) ratio of 20% (w/v) and then dissolving at 60° C. for 18 hours.

Figure 12:
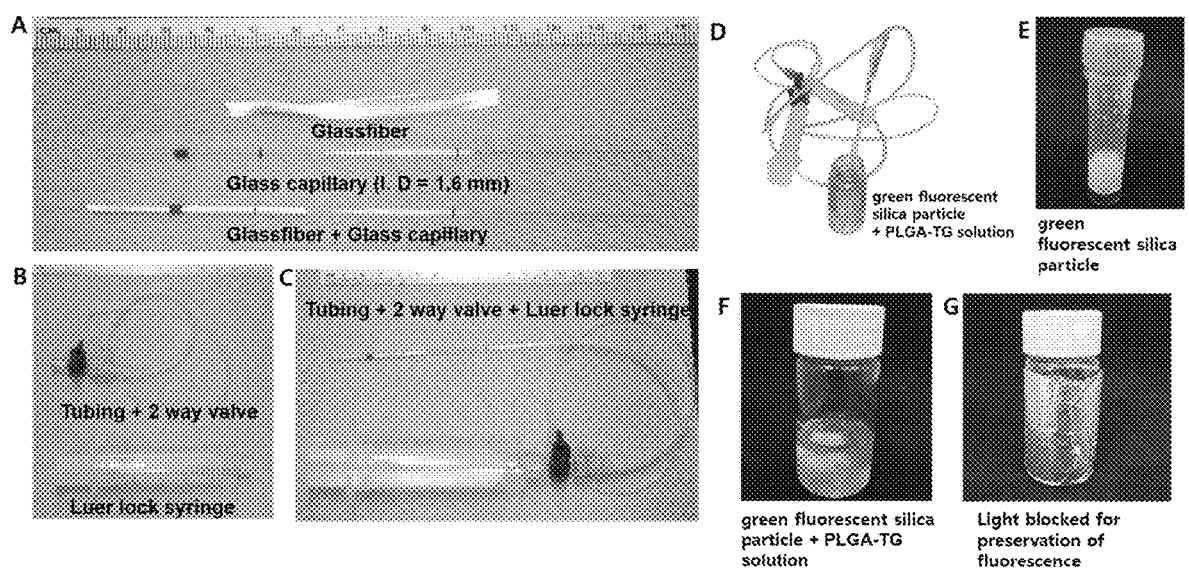
FIG. 12 shows photographs illustrating a method for preparing a porous nerve conduit containing a fluorescent nanoparticle. A shows glass fibers, a glass capillary and a glass capillary into which glass fibers are inserted, B shows a silicone tube coupled with a 2-way valve and a Luer lock syringe, C shows a silicone tube coupled with a 2-way valve and a Luer lock syringe, D shows application of vacuum into a glass tube using a syringe, E shows a green fluorescent silica particle stock solution, F shows a mixture solution of a green fluorescent silica particle and 20% (w/v) PLGA-TG, and G shows a mixture solution of a green fluorescent silica particle and 20% (w/v) PLGA-TG mixture solution with light blocked for preservation of fluorescence.

After transferring a 50 mg/mL stock solution of a green fluorescent silica nanoparticle (particle size: 500 nm, Sicastar®-greenF, micromod Partikeltechnologie, Germany) (FIG. 12E) of an amount corresponding to 1/50 of the volume of the 20% (w/v) PLGA-TG solution (e.g., when the volume of the 20% (w/v) PLGA-TG solution is 5 mL, the volume of the green fluorescent silica particle stock solution is 100 µL) to a 1.5-mL tube, centrifugation was performed at a speed of 8,000 rpm or lower for 30 seconds. Then, distilled water was removed from the green fluorescent silica particle stock solution suspended in the distilled water by removing the supernatant. After the removal of the distilled water, the green fluorescent silica particle was resuspended in a small amount (100 µL or less) of a TG stock solution and then completely mixed with the 20% (w/v) PLGA-TG solution (working concentration: 1 mg/mL) (FIG. 12F). The prepared mixture solution of the green fluorescent silica particle and the 20% (w/v) PLGA-TG was blocked from light for preservation fluorescence (FIG. 12G).

A glass capillary with an inner diameter of 1.6 mm and a length of 13 cm was heated at the center portion to form a bottleneck, thereby forming upper and lower channels sloped with a discontinuous angle. The lower channels were formed to have smaller diameters than the upper channel. Then, 7000-8500 strands of a water-soluble glass fiber ($50P_2O_5$-$20CaO$-$30Na_2O$ in mol % (1100° C., 800 rpm)) with diameters of 10-20 µm were cut to 5-6 cm and inserted densely into the upper channels of the glass tube along the axis direction (FIG. 12A).

A pressure device was prepared by connecting a Luer lock syringe equipped with a silicone tube of an inner diameter of 0.8 mm and a length of 15 cm, coupled with a 2-way valve, to the upper channels of the glass fiber-inserted glass tube (FIG. 12B and FIG. 12C).

Figure 11:
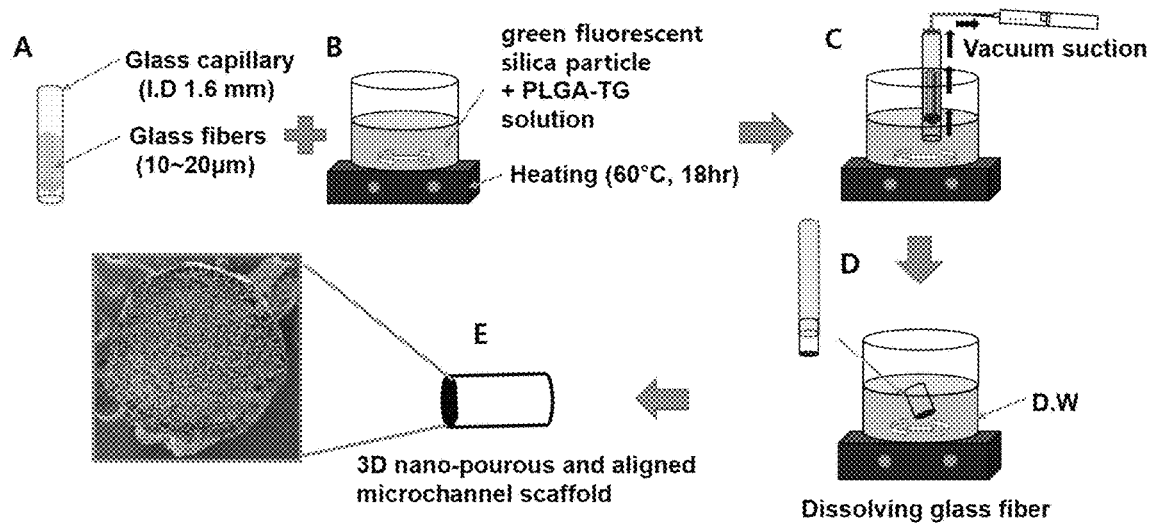
FIG. 11 schematically shows a method for preparing a nerve conduit containing a fluorescent nanoparticle according to an exemplary embodiment of the present disclosure.

After immersing the lower channels of the glass tube in the mixture solution of the green fluorescent silica particle and the 20% (w/v) PLGA-TG at room temperature, vacuum was repeatedly applied into the glass tube using a syringe such that the mixture solution was completely infiltrated into the void space between the glass fibers (FIG. 11C and FIG. 12D).

The PLGA-TG solution-infiltrated glass fibers were separated from the glass tube using a wire with a diameter of 1.5 mm and a length of 15 cm and, immediately thereafter, completely immersed in distilled water (DW) at 10-20° C. for at least 24 hours (FIG. 11D), so that the glass fibers were completely dissolved, and about 7,000-8,500 (7,777±716.2) microchannels of the PLGA containing the green fluorescent silica particle, with diameters of 10-20 μm (16.54±3.6 μm), were formed in the space where the glass fibers had been dissolved (FIG. 11E). The microchannels were formed as the glass fibers were dissolved in the water at 10-20° C. and the PLGA containing the green fluorescent silica particle was cured at the same time. And, the infiltrated glass fibers were completely dissolved by the DW while they were immersed in the DW. The microchannels were formed as the hydrophobic polymer PLGA was contacted with the DW in the space formed as the glass fibers were dissolved and then cured. Also, micropores were formed inside the microchannels as the water-miscible solvent was mixed with the water and released from the microchannels. Because the TG released from the nerve conduit had a higher density than the DW, it was submerged like heat haze in the DW.

After the glass fibers and the TG were removed through the treatment with DW, the prepared porous microchannels formed of the green fluorescent silica particle and the PLGA, i.e., the nerve conduit, was frozen in liquid nitrogen for about 30 seconds, cut to a desired size and then shaped into a desired shape.

2-2: Fluorescence Emission from Nerve Conduit

Figure 13:
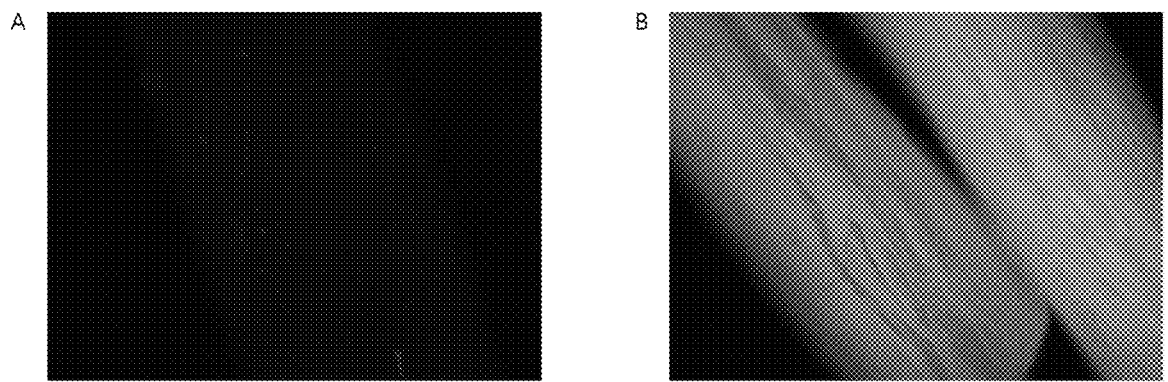
FIG. 13 shows fluorescence microscopic images of a nerve conduit not containing a fluorescent nanoparticle (A) and a nerve conduit containing a fluorescent nanoparticle (B).

Fluorescence emission from the nerve conduit containing a fluorescent nanoparticle prepared in Example 2-1 was observed using a fluorescence microscope. As seen from FIG. 13, the nerve conduit containing a fluorescent nanoparticle (Example 2-1) exhibited green fluorescence whereas the nerve conduit not containing a fluorescent nanoparticle (Example 1-1) did not exhibit green fluorescence.

Figure 14:
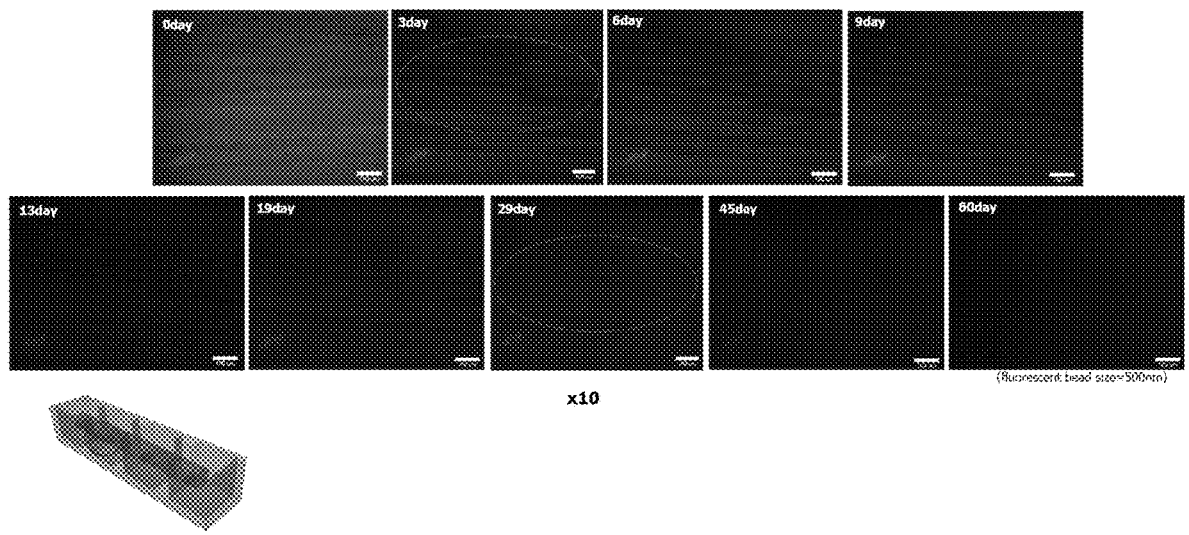
FIG. 14 shows fluorescence microscopic images of a nerve conduit containing a fluorescent nanoparticle kept at the same location under an in-vitro environment for 60 days.
Figure 15:
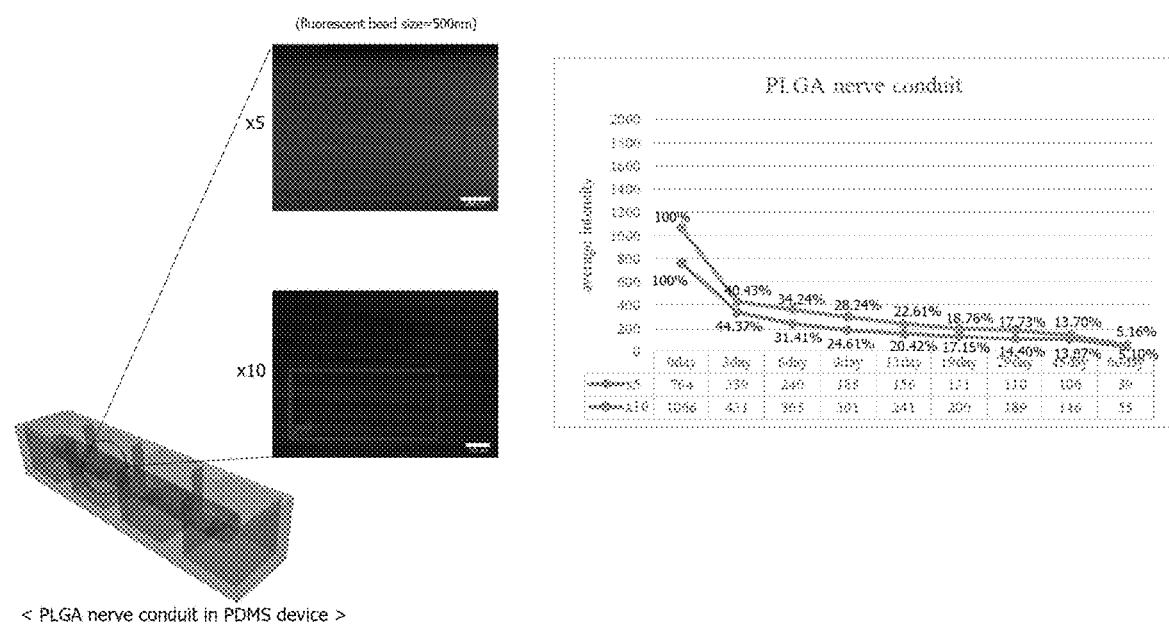
FIG. 15 shows the change in fluorescence intensity of a fluorescent nanoparticle for 60 days.

When the nerve conduit containing a fluorescent nanoparticle was imaged at the same location under an in-vitro environment for 60 days at a magnification of ×10, the fluorescence emission from the nerve conduit decreased with time as the fluorescent nanoparticle was degraded (FIG. 14). The fluorescence intensity of the fluorescent nanoparticle decreased greatly initially. 60 days later, the intensity was decreased to 5.10% at a magnification of ×5 and to 5.16% at a magnification of ×10 (FIG. 15). In FIG. 14 and FIG. 15, the "PDMS device" is a device used to fix the nerve conduit for the in-vitro experiment. A method for fixing the nerve conduit to the PDMS device is well known in the related art. To describe briefly, a mold of a desired shape is prepared first using a 3D printer, etc. and a PDMS solution is poured into the mold and then hardened.

Figure 16:
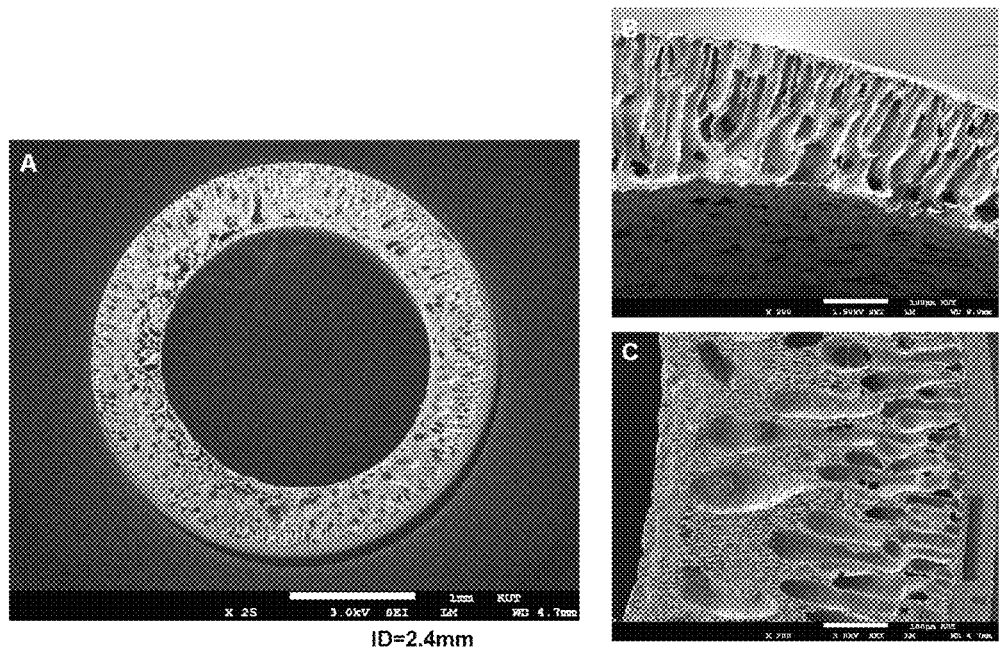
FIG. 16 shows transverse cross-sectional SEM images of a biocompatible polymer tube with micropores formed in which a nerve conduit according to the present disclosure is inserted (A) and magnified images showing parts of the tube (B, C).

Example 3: Nerve Regeneration after Transplantation of Nerve Conduit in Peripheral Nerve Injury Model A nerve conduit (diameter 1.6 mm, length 16 mm) was prepared by the method of Example 1-1. Then, a polycaprolactone (PCL) tube for inserting the nerve conduit was prepared. The PCL tube was prepared by the following method. A glass tube with an outer diameter of 1.6-1.7 mm was immersed in a 15% (w/v) PCL-TG solution so as to form a thin PCL-TG coat on the surface of the glass tube. Then, the PCL-TG-coated glass tube was immersed in DW, so that the PCL polymer was contacted with the water and then cured and micropores were formed in the hydrophobic polymer as the TG was mixed with the DW and released from the hydrophobic polymer. After removing the glass tube by pushing or pulling with forceps, followed by freezing in liquid nitrogen for 30 seconds and cutting to a length of 18 mm, a PCL tube was completed. FIG. 16 shows the prepared PCL tube having micropores formed.

Figure 17:
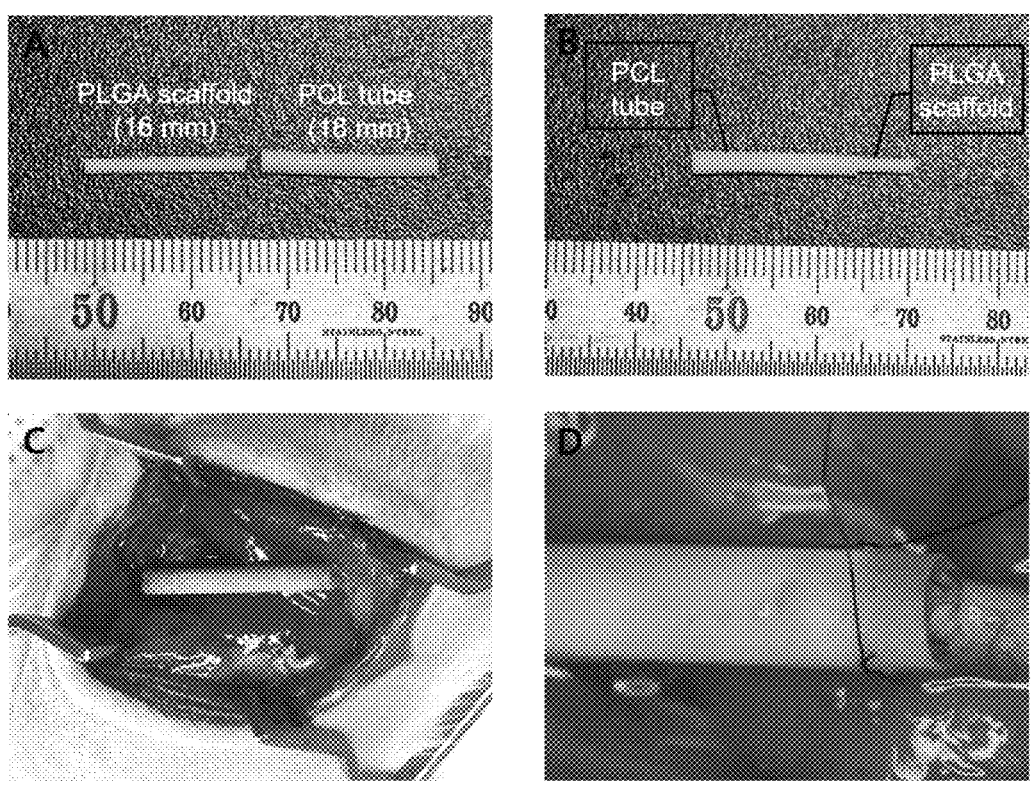
FIG. 17 illustrates an in-vivo experiment procedure for confirming the nerve regeneration effect of a nerve conduit according to the present disclosure. A shows a PCL tube and a PLGA nerve conduit prepared for an in-vivo experiment, B shows an image of a nerve conduit inserted in the PCL tube, and C shows image of a 16-mm nerve conduit inserted after cutting the sciatic nerve of a rat.

The nerve conduit prepared by the method of Example 1-1 was inserted to the polycaprolactone (PCL) tube with a diameter of 1.6-1.7 mm and a length of 18 mm (FIGS. 17, A and B). After removing the sciatic nerve (length 16 mm) of a 12-week-old female Sprague-Dawley rat at 5 mm below the hip joint, the nerve conduit was transplanted into the damaged area (FIG. 17C). In order to prevent the nerve conduit from being separated from the nerve, the both ends of the nerve conduit were sutured to the cut nerve terminals using a suture (10-0:0.02-0.029 mm thick nylon suture) (FIG. 17D).

As a control group, autografting was conducted after removing the sciatic nerve (length 16 mm) of a 12-week-old female Sprague-Dawley rat at 5 mm below the hip joint. The autografting was conducted by inverting the distal and proximal parts of the cut nerve and suturing with a 10-0 suture.

Figure 18:
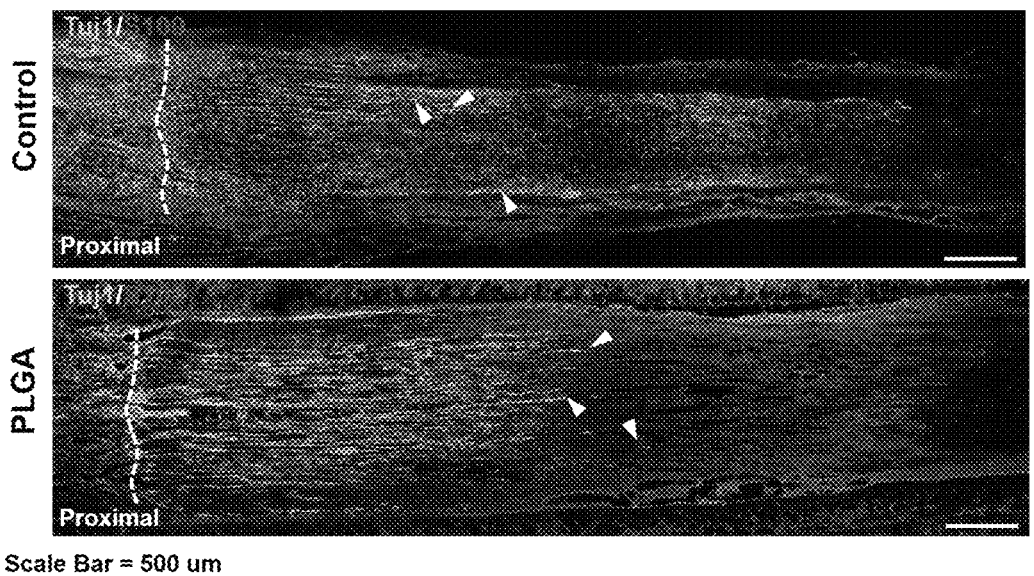
FIG. 18 shows a result of immunohistochemical staining of an animal of a peripheral nerve injury model autografted with or without (control) transplantation of a nerve conduit observed by confocal microscopy. The images are merged images of mouse Tuj1 monoclonal antibody staining and rabbit S100 polyclonal antibody staining.

Then, immunostaining was conducted to check the growth of the sciatic nerve. 2 weeks after the transplantation, the sciatic nerve containing the 18-mm long graft was taken out and fixed in 4% paraformaldehyde. Then, after treating with 30% sucrose for 3 days, the tissue was sliced to 16-μm thick sections. Mouse Tuj1 monoclonal antibody was used for staining of the neuronal axons and rabbit S100 polyclonal antibody was used for staining of the Schwann cells. The tissue sections were observed with a confocal microscope and the result is shown in FIG. 18. FIG. 18 shows merged images of mouse Tuj1 monoclonal antibody staining and rabbit S100 polyclonal antibody staining. As seen from FIG. 18, the growth of axons and Schwann cells along the channels at the proximal part of the nerve conduit was confirmed both in the autografted animal (control) and the animal in which the nerve conduit of the present disclosure was inserted. However, the animal in which the nerve conduit of the present disclosure was inserted showed higher peripheral nerve regeneration efficiency than the control group.

Example 4: Nerve Regeneration after Transplantation of Nerve Conduit in Central Nerve Injury (Transection) Model A nerve conduit (diameter 2.2 mm, length 5 mm) was prepared by the method of Example 1-1.

Figure 19:
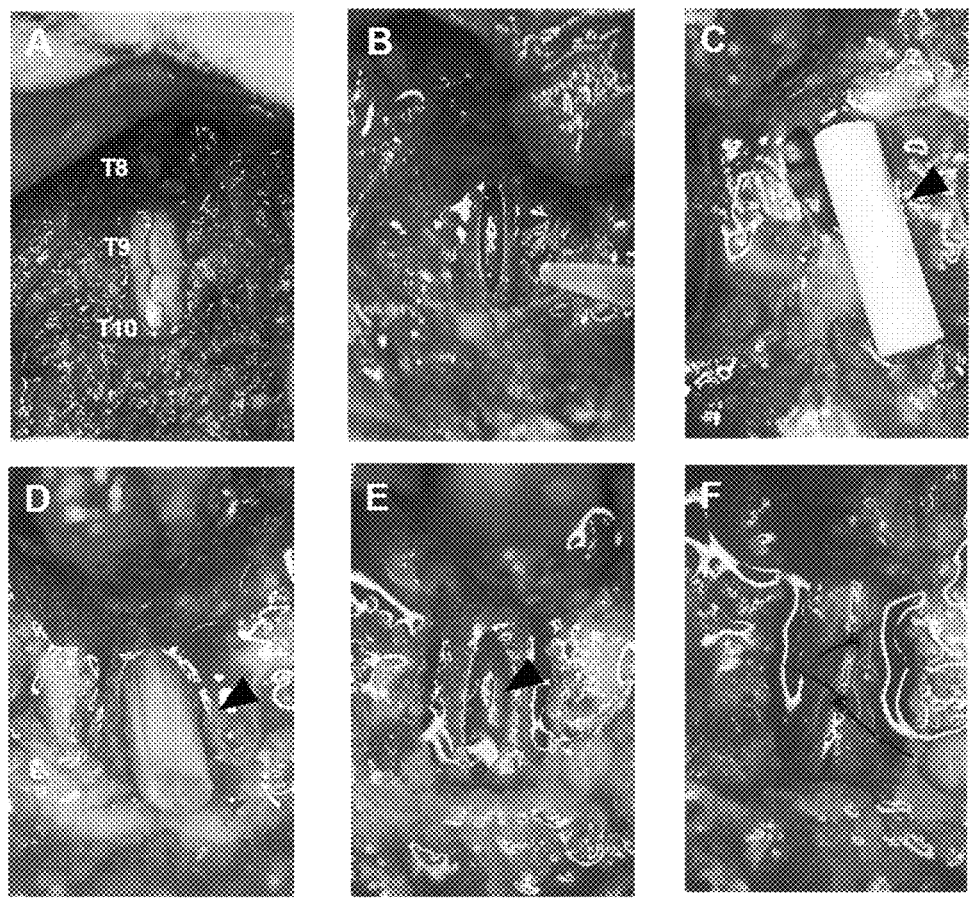
FIG. 19 shows a procedure of inserting a nerve conduit in a complete spinal cord transection model.

A central nerve injury model was prepared using a 12-week-old female Sprague-Dawley rat and the nerve conduit was transplanted (FIG. 19). First, laminectomy for transplanting the nerve conduit was performed on the ninth and tenth thoracic vertebrae (FIG. 19A). Then, after cutting open the dura mater of spinal cord and completely removing 5 mm of the spinal cord (FIG. 19B), the nerve conduit was transplanted at the spinal cord-removed part (FIG. 19C, 19D, 19E). After the transplantation of the nerve conduit, the dura mater was sutured using a suture (10-0:0.02-0.029-mm thick nylon suture) (FIG. 19F). A spinal cord transection model in which the nerve conduit was not transplanted was used as a control group.

Then, immunostaining was conducted to check the growth of the central nerve. 2 weeks after the transplantation, the central nerve containing the 5-mm long graft was taken out and fixed in 4% paraformaldehyde. Then, after treating with 30% sucrose for 3 days, the tissue was sliced to 16-μm thick sections. Mouse Tuj1 monoclonal antibody was used for staining of the neuronal axons of the tissue sections. The tissue sections were observed with a confocal microscope and the result is shown in FIG. 20 and FIG. 21.

Figure 20:
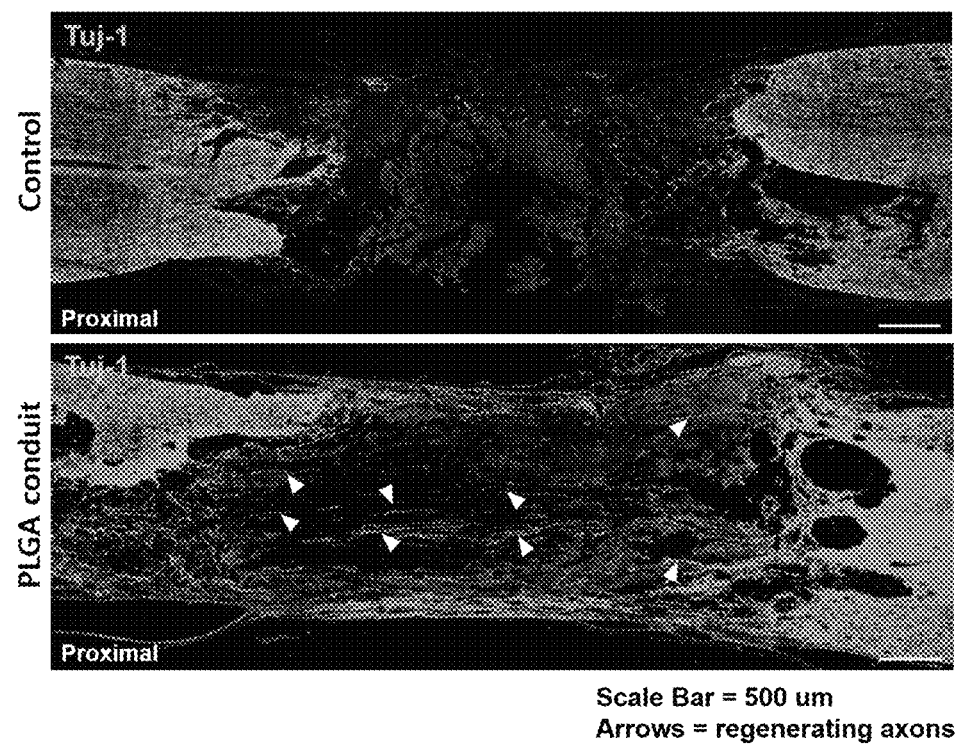
FIG. 20 shows a result of immunohistochemical staining of an animal of a complete spinal cord transection model 2 weeks after transplantation with or without (control) transplantation of a nerve conduit.

FIG. 20 shows a result of immunohistochemical staining of the animal of a complete spinal cord transection model 2 weeks after the transplantation with or without (control) transplantation of the nerve conduit. From FIG. 20, axons (arrows) regenerating across the damaged area inside the transplanted nerve conduit are observed. In contrast, axon regeneration was not observed in the control group in which the nerve conduit was not transplanted.

Figure 21:
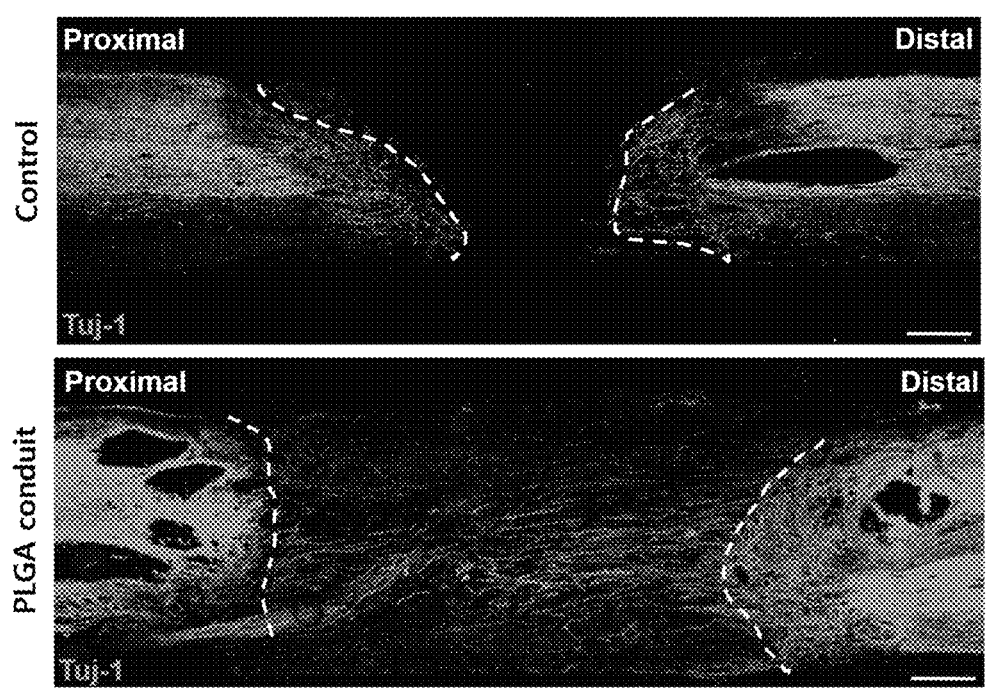
FIG. 21 shows a result of immunohistochemical staining of an animal of a complete spinal cord transection model 16 weeks spinal cord transection model 16 weeks after transplantation with or without (control) transplantation of a nerve conduit.

FIG. 21 shows a result of immunohistochemical staining of the animal of a complete spinal cord transection model 16 weeks after the transplantation autografting with or without (control) transplantation of the nerve conduit. From FIG. 21, axons regenerating across the damaged area inside the transplanted nerve conduit are observed. In contrast, axon regeneration was not observed in the control group in which the nerve conduit was not transplanted.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A method for preparing a nerve regeneration device, the method comprising:
    preparing a porous nerve conduit having a microchannel structure with micropores formed by:
        a step of inserting a plurality of water-soluble glass fibers into a container having upper and lower channels;
        a step of injecting a polymer material for a nerve conduit comprising a hydrophobic biocompatible polymer and a water-miscible organic solvent into the container in which the plurality of water-soluble glass fibers are inserted;
        a step of infiltrating the polymer material between the water-soluble glass fibers by applying vacuum to the upper channel;
        a step of separating the water-soluble glass fibers with the polymer material infiltrated from the container; and
        a step of forming a microchannel structure with micropores, comprising:
            immersing the separated water-soluble glass fibers with the polymer material in water; and
            dissolving the glass fibers, wherein the microchannel structure is formed in the space where the glass fibers were dissolved, and micropores are formed by mixing the water-miscible organic solvent with the water and releasing the water-miscible organic solvent from the polymer material,
        wherein the micropores are created in the microchannel structure where the water-miscible organic solvent was released from the polymer material,
        wherein the lower channel has a smaller diameter than the upper channel and the container is sloped with a discontinuous angle,
    wherein the polymer material for a nerve conduit is one in which the hydrophobic biocompatible polymer is dissolved in the water-miscible organic solvent at a concentration of 10-40 weight/volume % (w/v %),
    preparing a biocompatible polymer tube having micropores by:
        a step of immersing a forming tube in a mixture solution of a hydrophobic biocompatible polymer and a water-miscible organic solvent to form a thin coat on the forming tube,
        a step of curing the biocompatible polymer coat by immersing the coated forming tube in water, and
        a step of removing the biocompatible polymer tube from the forming tube, and
    inserting the nerve conduit having a microchannel structure with micropores into the biocompatible polymer tube having micropores to form the nerve regeneration device.

2. The method for preparing a porous nerve regeneration device of claim 1, wherein the porous nerve regeneration device is for regeneration of a central nerve or a peripheral nerve.

3. The method for preparing a porous nerve regeneration device of claim 1, wherein the polymer material for a nerve conduit is one in which a nanoparticle is further added in addition to the hydrophobic polymer and the water-miscible organic solvent.

4. The method for preparing a porous nerve regeneration device of claim 1, wherein the polymer material for a nerve conduit is in a solution state at room temperature.

5. The method for preparing a porous nerve regeneration device of claim 1, wherein the method for preparing a porous nerve conduit further comprises, after the step of dissolving the glass fibers:
    a step of cooling a nerve conduit formed after the glass fibers are dissolved with liquid nitrogen; and
    a step of shaping the cooled nerve conduit by cutting.

6. The method for preparing a porous nerve regeneration device of claim 1, wherein the container is formed of a transparent material so that the infiltration of the polymer material for a nerve conduit can be checked visually.

7. The method for preparing a porous nerve regeneration device of claim 1, wherein the application of vacuum is repeated multiple times.

8. The method for preparing a porous nerve regeneration device of claim 1, wherein the hydrophobic biocompatible polymer is selected from a group comprising of polylactic acid (PLA), poly-L/D-lactide (PLDA), poly-L-lactic acid (PLLA), polyglycolic acid (PGA)), polydioxanone, polyhydroxybutyrate (PHB), polyhydroxyalkanoate (PHA), poly(lactic-co-glycolic acid) (PLGA), polycaprolactone (PCL), a copolymer thereof and a mixture thereof; and
    the water-miscible organic solvent is selected from a group comprising of ethanol, isopropyl alcohol, N-methyl-2-pyrrolidone, 2-pyrrolidone, glycerol, propylene glycol, polyethylene glycol, tetraglycol, glycerol formal, ethyl acetate, ethyl lactate, diethyl carbonate, propylene carbonate, acetone, methyl ethyl ketone, dimethyl sulfoxide, dimethyl sulfone, tetrahydrofuran, tetrahydrofurfuryl alcohol, succinic acid diethyl ester, triethyl citrate, dibutyl sebacate, dimethylacetamide, lactic acid butyl ester, propylene glycol diacetate, diethylene glycol monoethyl ether and a mixture thereof.

9. The method for preparing a porous nerve regeneration device of claim 3, wherein the nanoparticle is a fluorescent nanoparticle.

10. A method for preparing a nerve regeneration device, the method comprising:
preparing a porous nerve conduit having a microchannel structure with micropores formed by:
inserting a plurality of water-soluble glass fibers into a container having upper and lower channels;
injecting a polymer material for a nerve conduit comprising a hydrophobic biocompatible polymer and a water-miscible organic solvent into the container in which the plurality of water-soluble glass fibers are inserted;
infiltrating the polymer material between the glass fibers by applying vacuum to the upper channel;
separating the water-soluble glass fibers with the polymer material infiltrated from the container;
forming a microchannel structure by dissolving the glass fibers; and
forming micropores in the microchannel structure by separating the water-miscible organic solvent from the hydrophobic biocompatible polymer,
wherein the lower channel has a smaller diameter than the upper channel and the container is sloped with a discontinuous angle,
wherein the polymer material for a nerve conduit is one in which the hydrophobic biocompatible polymer is dissolved in the water-miscible organic solvent at a concentration of 10-40 weight/volume % (w/v %),
preparing a biocompatible polymer tube having micropores by:
a step of immersing a forming tube in a mixture solution of a hydrophobic biocompatible polymer and a water-miscible organic solvent to form a thin coat on the forming tube,
a step of curing the biocompatible polymer coat by immersing the coated forming tube in water, and
a step of removing the biocompatible polymer tube from the forming tube, and
inserting the nerve conduit having a microchannel structure with micropores into the biocompatible polymer tube having micropores to form the nerve regeneration device.

11. The method for preparing a porous nerve regeneration device of claim 10, wherein the porous nerve regeneration device is for regeneration of a central nerve or a peripheral nerve.

12. The method for preparing a porous nerve regeneration device of claim 10, wherein the polymer material for a nerve conduit is one in which a nanoparticle is further added in addition to the hydrophobic polymer and the water-miscible organic solvent.

13. The method for preparing a porous nerve regeneration device of claim 10, wherein the polymer material for a nerve conduit is in a solution state at room temperature.

14. The method for preparing a porous nerve regeneration device of claim 10, wherein the method for preparing a porous nerve conduit further comprising:
cooling a nerve conduit formed after the glass fibers are dissolved with liquid nitrogen; and
shaping the cooled nerve conduit by cutting.

15. The method for preparing a porous nerve regeneration device of claim 10, wherein the container is formed of a transparent material so that the infiltration of the polymer material for a nerve conduit can be checked visually.

16. The method for preparing a porous nerve regeneration device of claim 10, wherein the application of vacuum is repeated multiple times.

17. The method for preparing a porous nerve regeneration device of claim 10, wherein the hydrophobic biocompatible polymer is selected from a group comprising of polylactic acid (PLA), poly-L/D-lactide (PLDA), poly-L-lactic acid (PLLA), polyglycolic acid (PGA)), polydioxanone, polyhydroxybutyrate (PHB), polyhydroxyalkanoate (PHA), poly (lactic-co-glycolic acid) (PLGA), polycaprolactone (PCL), a copolymer thereof and a mixture thereof; and
the water-miscible organic solvent is selected from a group comprising of ethanol, isopropyl alcohol, N-methyl-2-pyrrolidone, 2-pyrrolidone, glycerol, propylene glycol, polyethylene glycol, tetraglycol, glycerol formal, ethyl acetate, ethyl lactate, diethyl carbonate, propylene carbonate, acetone, methyl ethyl ketone, dimethyl sulfoxide, dimethyl sulfone, tetrahydrofuran, tetrahydrofurfuryl alcohol, succinic acid diethyl ester, triethyl citrate, dibutyl sebacate, dimethylacetamide, lactic acid butyl ester, propylene glycol diacetate, diethylene glycol monoethyl ether and a mixture thereof.

18. The method for preparing a porous nerve regeneration device of claim 12, wherein the nanoparticle is a fluorescent nanoparticle.

\* \* \* \* \*